United States Patent [19]

Phillips

[11] 3,988,321

[45] Oct. 26, 1976

[54] SUBSTITUTED DICHLOROSULFENAMIDES AND THEIR MANUFACTURE

[75] Inventor: Wendell Gary Phillips, Olivette, Mo.

[73] Assignee: Monsanto Company, St. Louis, Mo.

[22] Filed: Jan. 28, 1975

[21] Appl. No.: 544,733

Related U.S. Application Data

[62] Division of Ser. Nos. 355,836, April 30, 1973, Pat. No. 3,888,925, and Ser. No. 159,034, July 1, 1971, Pat. No. 3,766,172.

[52] U.S. Cl. .................. 260/239 B; 260/293.69; 260/293.85; 260/326.42; 260/326.25; 260/326.37; 260/326.82; 260/558 S; 260/293.73; 71/88; 424/244; 424/267; 424/279; 424/311; 424/320; 424/325

[51] Int. Cl.² ............. C07D 295/22; C07D 223/04; C07D 207/48; C07D 211/96

[58] Field of Search ............ 260/326.5 SF, 293.73, 260/239 B, 326.82

[56] References Cited

UNITED STATES PATENTS 3,887,571  6/1975  Gattuso .................... 260/239 B

Primary Examiner—Alton D. Rollins
Assistant Examiner—Mark L. Berch
Attorney, Agent, or Firm—Richard H. Shear

[57] ABSTRACT

Substituted dichlorosulfenamides are prepared from dichloromethyl sulfenyl chlorides by reaction with a primary or secondary amine. The substituted dichlorosulfenamides are pesticidally active and particularly useful as pre-emergent herbicides.

2 Claims, No Drawings

SUBSTITUTED DICHLOROSULFENAMIDES AND THEIR MANUFACTURE

This is a division of application Ser. No. 355,836, (now U.S. Pat. No. 3,888,925), filed Apr. 30, 1973, and Ser. No. 159,034, filed July 1, 1971, now U.S. Pat. No. 3,766,172.

This invention relates to substituted dichlorosulfenamides of the formula

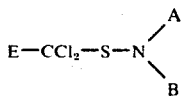

and their manufacture from the corresponding dichloromethyl sulfenyl chlorides of the formula E—CCl$_2$—S—Cl and an amine of the formula

wherein E— is

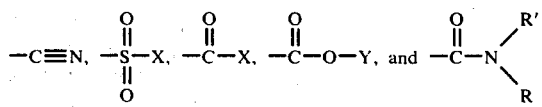

X is phenyl, halophenyl or lower alkyl phenyl, Y is lower alkyl or benzyl, R is lower alkyl, lower alkoxyalkyl, or lower alkoxy, R' is phenyl, halophenyl, lower alkyl phenyl, lower alkyl, lower alkoxyalkyl, or lower alkoxy or R and R' when taken together are alkylene of the empirical formula C$_n$H$_{2n}$ wherein n is an integer from 4 through 8, inclusive, and having from 4 through 8 carbons in a continuous chain between the nitrogen terminal valence bonds, A is hydrogen, methyl lower alkenyl, methyl lower alkynyl, lower alkyl, lower alkoxyalkyl, or lower alkoxy and B is methyl lower alkenyl, methyl lower alkynyl, phenyl, halophenyl, lower alkyl phenyl, lower alkyl, lower alkoxyalkyl, or lower alkoxy or A and B when taken together are alkylene of the empirical formula C$_n$H$_{2n}$ wherein n is an integer from 4 through 8, inclusive, and having from 4 through 8 carbons in a continuous chain between the nitrogen terminal valence bonds.

Lower alkyl is alkyl having from 1 to 5 carbons. Examples of lower alkyl include, but are not limited to, methyl, ethyl, propyl, isopropyl, butyl, sec-butyl, isobutyl, tert-butyl, and pentyl.

Lower alkoxy have from 1 to 5 carbons. Examples of alkoxy include, but are not limited to, methoxy, ethoxy, propoxy, butoxy and pentoxy. Lower alkoxyalkyl have from 2 to 8 carbons. Examples of lower alkoxyalkyl are propoxymethyl, butoxybutyl, butoxyethyl, methoxymethyl, and ethoxypropyl.

Halo is a halogen selected from the group consisting of fluorine, chlorine, bromine and iodine.

Lower alkenyl and lower akynyl have from 2 through 4 carbons. Examples of lower alkenyl include, but are not limited to vinyl, allyl and crotyl. Examples of lower alkynyl include, but are not limited to, acetenyl, 2-propynyl (propargyl), 1-methyl-2-propynyl, 2-butynyl, and 3-butynyl. In compounds of this invention lower alkenyl and lower alkynyl are attached to the nitrogen of the amine by a methylene group so that the carbon adjacent to the nitrogen is always saturated.

Exemplary of halophenyl and lower alkyl phenyl are substituted phenyls of the formula

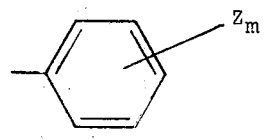

wherein Z is halo, trihalomethyl, or lower alkyl and m is an integer from 1 through 3, inclusive.

Examples of alkylene of the empirical formula C$_n$H$_{2n}$ wherein n is an integer from 4 through 8, inclusive, and having from 4 through 8 carbons in a continuous chain between the nitrogen terminal valence bonds include but are not limited to pyrrolidinyl, piperidinyl, hexamethyleneimino, heptamethyleneimino, octamethyleneimino, 2-ethylpyrrolidinyl, 3-butylpyrrolidinyl, 2,5-dimethylpyrrolidinyl, 2,5-diethylpyrrolidinyl, 3,4-dimethylpyrrolidinyl, 2-pipecolinyl, 3-pipecolinyl, 4-pipecolinyl, 2,6-dimethylpiperidinyl, 2-ethyl-6-methylpiperidinyl, 2-propylpiperidinyl, 3-methylhexamethyleneimino, 3,4-dimethylhexamethyleneimino, and the various isomeric forms thereof.

The compounds of this invention are conveniently and efficiently prepared by the reaction of about 1 molecular proportion of a dichloromethyl sulfenyl chloride of the formula E-CCl$_2$-S-Cl and 2 molecular proportions of an amine of the formula

wherein E, A and B have the aforementioned significance. The reaction is postulated to proceed as follows:

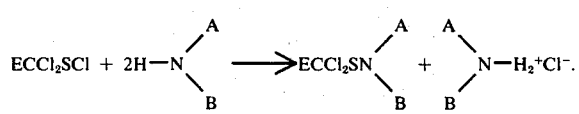

One of the molecular proportions of the amine is consumed by salt formation with the liberated hydrochloride. Where the amine is of high value, difficult to obtain, or for any reason it is desired to minimize the amount of amine used, it may be preferred to conduct the reaction in the presence of another HCl scavenger. In this embodiment it is postulated that the reaction proceeds as follows:

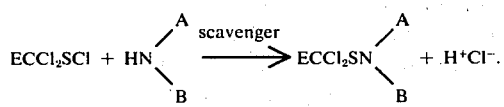

The scavenger must be present in at least an equimolecular amount as compared to the substituted sulfenyl chloride. Generally not more than twice the equimolecular amount of scavenger is useful although the maximum amount is not critical. The type of scavenger is not critical to the invention so long as it does not interfere with the reaction of the substituted amine and the substituted sulfenyl chloride. Preferred scavengers are trialkyl amines. More preferred trialkylamines have from 2 through 5 carbons in the alkyl group.

The reaction mass may consist only of the aforedescribed reactants and their reaction products or it may contain other components in addition such as diluents, other inert materials and solvents, i.e., common organic liquids which are inert under the reaction conditions and which may dissolve one or more of the reactants or products of the reaction, which solvents are exemplified by but not limited to aliphatic hydrocarbons, such as pentane, hexane, mineral spirits, etc., aromatics such as benzene, toluene, xylenes, etc., ethers such as diethyl ether, diisopropyl ether, petroleum ether, etc., esters such as methyl acetate, ethyl acetate, propyl acetate, etc., and other organics such as tetrahydrofurane, etc. The hydrochloride salt by-product is generally not soluble in the above solvents. Accordingly, the insoluble salt usually forms a precipitate in the reaction mass and may be easily removed by filtration. When filtration is not desired or the salt is soluble in the solvent, the salt may be readily removed from the reaction mass by extraction with water.

The reaction is normally carried out at a temperature above the freezing point of the system but preferably not above its boiling point. Still more preferably, the reaction is carried out at temperatures of from about 0° Centigrade (° C.) to about 60° C. The reaction is usually carried out at atmospheric pressure, but higher or lower pressures may be utilized if equipment and other factors favor such higher or lower pressures. The reaction may be carried out in an open vessel or under reflux.

Substituted 1,1-dichlorosulfenamides of this invention are useful as biocides. Exemplary of such biocidal uses for these products is the control of nematodes, arachnids, arthropods and insects as well as eradication of noxious weeds. These compounds are particularly useful as pre-emergent and contact herbicides.

Pre-emergent and contact herbicidal compounds are useful in the selective killing of weeds in crops. In using the compounds of the present invention as pre-emergent and contact herbicides, the compounds can be used alone or in combination with a material referred to in the art as an adjuvant in liquid or solid form. Herbicidal formulations are prepared by admixing the compound which is the active ingredient of the formulation with an adjuvant including diluents, extenders, carriers and conditioning agents to provide compositions in the form of finely-divided particulate solids, granules, pellets, solutions, dispersions or emulsions. Thus, the active ingredient can be used with an adjuvant such as a finely-divided particulate solid, a liquid of organic origin, water, a wetting agent, dispersing agent, an emulsifying agent or any suitable combination of these. The herbicidal formulations usually contain from about 0.01 percent to about 99 percent by weight of the active ingredient. Application of these formulations to the soil or growth media can be carried out by simply admixing with the soil, by applying to the surface of the soil and thereafter dragging or discing into the soil to the desired depth, or by employing a liquid carrier to accomplish the penetration and impregnation. The application of liquid and particulate solid herbicidal formulations to the surface of soil or to above ground portions of plants can be carried out by conventional methods, e.g. power dusters, boom and hand sprayers and spray dusters. The formulations can also be applied from airplanes as a dust or a spray because of their effectiveness at low dosages. In a further method, the distribution of the active ingredients in soil can be carried out by admixture with the water employed to irrigate the soil. In such procedures, the amount of water can be varied with the porosity and water holding capacity of the soil to obtain the desired depth of distribution of the active ingredients.

The exact amount of active ingredient to be employed is dependent upon the response desired in the plant as well as such other factors as the plant species and stage of development thereof, the specific soil and depth at which the active ingredients are distribution in the soil and the amount of rainfall as well as the specific active ingredient employed. In foliar treatment, the active ingredients are applied in amounts from about 1 to about 50 or more pounds per acre. In applications to soil for the control of the growth of germinant seeds, germinative seeds, emerging seedlings and established vegetation, the active ingredients are applied in amounts from about 0.1 to about 25 or more pounds per acre. It is believed that one skilled in the art can readily determine from the teachings of this specification the general procedure for any application.

Manufacture of dichloromethyl sulfenyl chlorides, used as starting materials in the preparation of the compounds of the present invention, is taught in my prior U.S. patent application Ser. Nos. 139,976 and 139,978 filed May 3, 1971, now U.S. Pat. Nos. 3,770,824 and 3,792,088, respectively and each entitled "Substituted Alpha, Alpha-Dichloro-Methane Sulfenyl Chlorides and Their Manufacture".

Amines used in the preparation of the compounds of the present invention are either known compounds or may be prepared by prior art methods from known compounds.

As illustrative of this invention, but not limitative thereof, is the following:

EXAMPLE 1

To a suitable reaction vessel equipped with an agitator is charged approximately 100 milliliters (ml.) of benzene, approximately 5.6 grams (g.), about 0.02 moles, of dichloro(diisopropylcarbamoyl) methyl sulfenyl chloride and approximately 2.52 g., about 0.04 moles, of pyrrolidine. A precipitate forms almost immediately. The mass is heated with stirring to about 70° C. and maintained at about 70° C. for about 1 hour (hr.). The mass is cooled to about room temperature, about 23° C., and the precipitate is removed by filtration. Thereafter the benzene is removed by distillation leaving an oily residue. The oil is dissolved in pentane and, upon cooling in dry ice, a yellow solid crystallizes out of the solution. The yellow solid is separated from the liquid by filtration, is found to have a melting point of about 50° to 53° C. and is identified as 2,2-dichloro-N,N-diisopropyl-2-(1-pyrrolidinylthio)acetamide

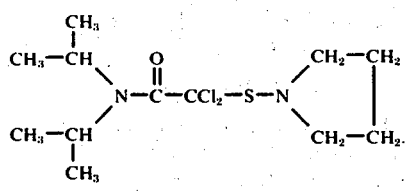

Calculated for $C_{12}H_{22}Cl_2N_2OS$: C, 46.00; H, 7.08; Found: C, 45.12; H, 7.13.

EXAMPLE 2

Following the procedure of Example 1 except that, in place of pyrrolidine, about 5.1 g. of octahydro-1H-azonine is charged to the vessel and the resultant product is identified as 2,2-dichloro-N,N-diisopropyl-2-(octahydro-1H-azonin-1-ylthio) acetamide

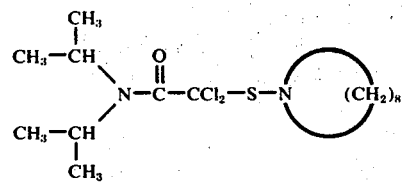

a white solid with a melting point of about 116° to 119° C.

Calculated for $C_{16}H_{30}Cl_2N_2OS$: C, 52.02; H, 8.19; Found: C, 52.24; H, 8.33.

EXAMPLE 3

Following the procedure of Example 1 except that, in place of pyrrolidine, about 4 grams of 2,5-dimethyl pyrrolidine is charged to the vessel and the resultant product is identified as 2,2-dichloro-N,N-diisopropyl-2-(2,5-dimethyl-1-pyrrolidinylthio)acetamide

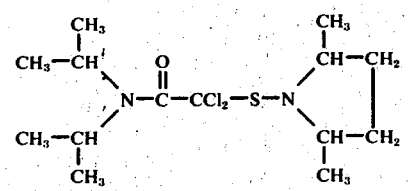

a white solid with a melting point of about 50° to 52° C.

Calculated for $C_{14}H_{26}Cl_2N_2OS$: C, 49.26; H, 7.68; Found: C, 49.30; H, 7.75.

EXAMPLE 4

To a suitable reaction vessel equipped with an agitator is charged about 200 ml. of diethyl ether, and approximately 2.5 g., about 0.02 moles, of octahydro-1H-azonine is added and dissolved in the ether. Approximately 3.2 g., about 0.01 moles, of 2-(chlorothio)-2,2-dichloro-N-isopropylacetanilide is then added and a precipitate forms almost immediately. The mass is stirred for about 2 hours, the precipitate is removed from the liquid by filtration and the ether is then removed by distillation. Petroleum ether is added to the remaining oil, the mass is cooled in dry ice, and crystallization is initiated by scratching the interior surface of the vessel below the liquid surface. Additional tan crystals are formed upon evaporation of the petroleum ether. The tan crystals are found to have a melting point of about 63° to 64° C. and are identified as 2,2-dichloro-N-isopropyl-2-(octahydro-1H-azonin-1-ylthio) acetanilide

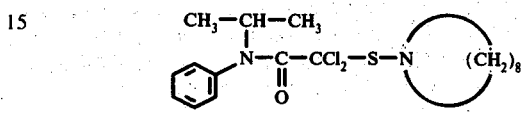

Calculated for $C_{19}H_{28}Cl_2N_2OS$: C, 56.57; H, 7.00; N, 6.94; Found: C, 57.05; H, 7.15; N, 6.89.

EXAMPLE 5

A suitable reaction vessel equipped with an agitator is charged with about 200 ml. of diethyl ether and about 3.12 g. of 2-(chlorothio)-2,2-dichloro-N-isopropylacetanilide is dissolved in the ether, before about 2.14 g. of N-methylaniline is added. The mass is stirred for about 1 hour and the precipitate which forms is removed by filtration. Any remaining ether is stripped from the liquid by vacuum distillation, the remaining solid is then washed with petroleum ether and the washings retained. The solid is identified as N-methylaniline hydrochloride. The retained washings are distilled to remove the petroleum ether and the remaining oil is identified as 2,2-dichloro-N-isopropyl-2-(N-methylanilinothio)acetanilide

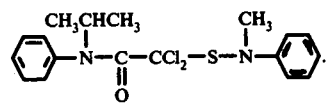

Calculated for $C_{18}H_{20}Cl_2N_2OS$: C, 56.4; H, 5.26; N, 7.31; Found: C, 56.30; H, 5.15; N, 7.48.

EXAMPLE 6

A suitable reaction vessel equipped with an agitator is charged with about 100 ml. of diethyl ether and approximately 3.12 g., about 0.01 moles, of 2-(chlorothio)-2,2-dichloro-N-isopropylacetanilide is dissolved in the ether before approximately 1.42 g., about 0.02 moles, of pyrrolidine is added. A precipitate forms immediately and, after the mass is stirred for about 5 minutes, is removed by filtration. The remaining liquid is distilled to remove the ether and the residual is crystallized upon scratching. The crystals have a melting point of about 77° to 79° C. and are identified as 2,2-dichloro-N-isopropyl-2-(1-pyrrolidinylthio) acetanilide

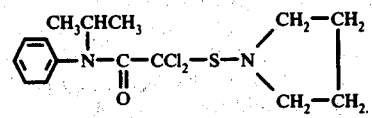

Calculated for C₁₅H₂₀Cl₂N₂OS: C, 51.87; H, 5.8; N, 8.07; Found: C, 51.73; H, 5.90; N, 8.07.

EXAMPLE 7

To a suitable reaction vessel equipped with an agitator is charged about 100 ml. of benzene. Approximately 3.8 g. of 2-chlorothio-N-isopropyl-2,2,3′,4′-tetrachloroacetanilide and approximately 2 g. of diethylamine are then added and dissolved in the benzene. The mass is stirred for about ½ hour, the precipitate which forms is removed by filtration and the benzene is stripped from the remaining liquid by distillation. The residual oil is dissolved in pentane and cooled in dry ice. The precipitate which forms upon cooling is separated by filtration, found to have a melting point of about 82° to 84° C. and identified as 2-(diethylaminothio)-N-isopropyl-2,2,3′,4′-tetrachloroacetanilide

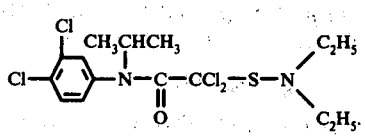

Calculated fo C₁₅H₂₀Cl₄N₂OS: C, 43.08; H, 4.82; N, 6.70; Found: C, 43.00; H, 4.84; N, 6.63.

EXAMPLE 8

Following the procedure of Example 7 except that, in place of diethylamine, about 2 grams of di-2-propenylamine is added and the residual oil is crystallized from petroleum ether rather than pentane, the resultant product, having a melting point of about 64° to 66° C., is identified as 2-(di-2-propenylaminothio)-N-isopropyl-2,2,3′,4′-tetrachloroacetanilide

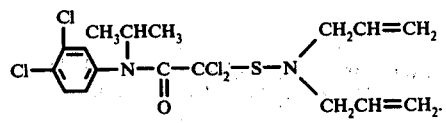

Calculated for C₁₇H₂₀Cl₄N₂OS: C, 46.17; H, 4.56; N, 6.33; Found: C, 46.18; H, 4.55; N, 6.30.

EXAMPLE 9

Following the procedure of Example 7 except that, in place of diethylamine, about 2.3 g. of hexahydro-1(2H)-azocine is added and the residual oil is dissolved in a mixture of about 90 percent by volume petroleum ether and about 10 percent by volume diethyl ether. Upon cooling in dry ice no precipitate appears but upon slow warming from about −70° C. a precipitate comes out which is isolated by filtration, is found to have a melting point of about 52° to 54° C. and is identified as 2-(hexahydro-1(2H)-azocinylthio)-N-isopropyl-2,2,3′,4′-tetrachloroacetanilide

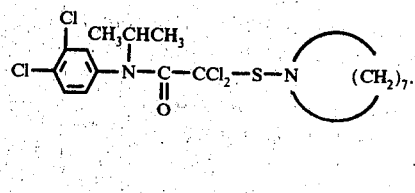

Calculated fo C₁₈H₂₄Cl₄N₂OS: C, 47.17; H, 5.28; N, 6.11; Found: C, 47.03; H, 5.11; N, 6.31.

EXAMPLE 10

To a suitable reaction vessel equipped with an agitator is charged about 100 ml. of benzene. Approximately 5.6 g. of dichloro(diisopropylcarbamoyl)methyl sulfenyl chloride is added and dissolved in the benzene. Approximately 1.7 g. of 1,1-dimethyl-2-propynylamine is added and a precipitate forms almost immediately. The mass is stirred overnight at ambient room temperature, about 23° C, and the precipitate is removed by filtration. The benzene is then removed leaving a residual oil. The oil is dissolved in pentane and cooled in dry ice. Upon cooling a precipitate appears which is separated from the liquid by filtration, dissolved in and recrystallized from petroleum ether, and separated from the petroleum ether by filtration. The white solid product, with a melting point of about 81 to 83° C. is identified as 2,2-dichloro-N,N-diisopropyl-2-[(1,1-dimethyl-2-propynyl)aminothio]acetamide

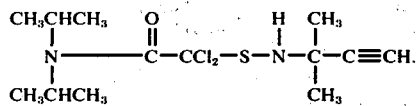

Calculated for C₁₃H₂₂Cl₂N₂OS: C, 48; H, 6.82; Found: C, 48.04; H, 6.95.

EXAMPLE 11

To a suitable reaction vessel equipped with an agitator is charged approximately 100 ml. of benzene and approximately 2.92 g., about 0.01 moles, of dichloro(-phenylsulfonyl)methyl sulfenyl chloride. After the chloride is dissolved in the benzene, approximately 2.54 g., about 0.02 moles, of octahydro-1H-azonine is added to the solution. The reaction mass is stirred for about 1 hour and the hydrochloride salt precipitate which forms is separated from the liquid by filtration. Solvent is removed by distillation leaving a residual solid. The residual solid is dissolved in petroleum ether and cooled in dry ice whereupon a precipitate forms. The precipitate which forms is separated from the ether by filtration, found to have a melting point of about 88° to 89° C., and identified as dichloro(octahydro-1H-azonin-1-ylthio)methyl benzenesulfinate

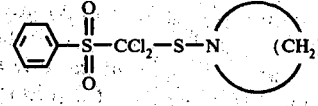

Calculated fo $C_{15}H_{21}Cl_2NO_2S_2$: C, 47.12; H, 5.54; N, 3.66; Found: C, 47.14; H, 5.39; N, 3.56.

EXAMPLE 12

The procedure of Example 11 is followed except that, in place of octahydro-1H-azonine, about 1.7 g. of 1,1-dimethyl-2-propynylamine is added. A residual oil is obtained which upon recrystallization forms a solid with a melting point of about 81° to 83° C. which is identified as dichloro[(1,1-dimethyl-2-propynyl-)aminothio]methyl benzenesulfinate

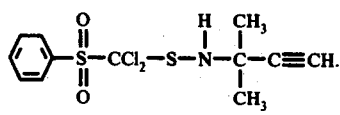

Calculated for $C_{12}H_{13}Cl_2NO_2S_2$: C, 42.61; H, 3.87; N, 4.14; Found: C, 42.57; H, 3.85; N, 4.07.

EXAMPLE 13

To a suitable reaction vessel equipped with an agitator is charged about 150 ml. of benzene and then approximately 7.4 g., about 0.02 moles, of 2-chlorothio-2,2-dichloro-2',6'-diethyl-N-methoxymethylacetanilide is added and dissolved in the benzene. Thereupon, approximately 2.8 g., about 0.04 moles, of pyrrolidine is added and a precipitate forms immediately. The mass is stirred for about 10 minutes and the precipitate is removed from the liquid by filtration. Benzene is stripped from the liquid remaining by distillation leaving a residual oil. The oil is dissolved in petroleum ether and cooled in dry ice whereupon a precipitate forms. The precipitate is removed from the liquid by filtration and dissolved again in petroleum ether. Upon cooling in dry ice again a precipitate is formed which is removed by filtration. The white solid is found to have a melting point of about 56° to 58° C. and identified as 2,2-dichloro-2',6'-diethyl-N-methoxymethyl-2-(1-pyrrolidinylthio)-acetanilide

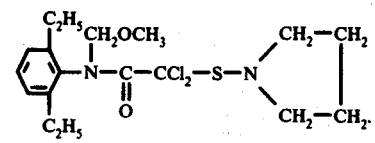

Calculated for $C_{18}H_{26}Cl_2N_2O_2S$: C, 53.33; H, 6.46; Found: C, 52.78; H, 6.51.

EXAMPLES 14 through 31

The procedure of Example 1 is followed except that, in place of about 5.6 g. of dichloro(N,N-diisopropylcarbamoyl)methyl sulfenyl chloride, an approximately equimolecular amount of the compound of Column A is charged and the product of Column B is obtained:

| Example | A | B |
| --- | --- | --- |
| 14 | N≡C—CCl$_2$—S—Cl | N≡CCl$_2$—S—N⟨(CH$_2$)$_4$⟩ |
| 15 | Br—C$_6$H$_4$—S(O)$_2$—CCl$_2$—S—Cl | Br—C$_6$H$_4$—S(O)$_2$—CCl$_2$—S—N⟨(CH$_2$)$_4$⟩ |
| 16 | 2,6-(CH$_3$)$_2$C$_6$H$_3$—S(O)$_2$—CCl$_2$—S—Cl | 2,6-(CH$_3$)$_2$C$_6$H$_3$—S(O)$_2$—CCl$_2$—S—N⟨(CH$_2$)$_4$⟩ |
| 17 | CF$_3$—C$_6$H$_4$—S(O)$_2$—CCl$_2$—S—Cl | CF$_3$—C$_6$H$_4$—S(O)$_2$—CCl$_2$—S—N⟨(CH$_2$)$_4$⟩ |
| 18 | 2,4,6-Cl$_3$C$_6$H$_2$—C(O)—CCl$_2$—S—Cl | 2,4,6-Cl$_3$C$_6$H$_2$—C(O)—CCl$_2$—S—N⟨(CH$_2$)$_4$⟩ |
| 19 | C$_6$H$_5$—C(O)—CCl$_2$—S—Cl | C$_6$H$_5$—C(O)—CCl$_2$—S—N⟨(CH$_2$)$_4$⟩ |
| 20 | CF$_3$—C$_6$H$_4$—C(O)—CCl$_2$—S—Cl | CF$_3$—C$_6$H$_4$—C(O)—CCl$_2$—S—N⟨(CH$_2$)$_4$⟩ |

| Example | A | B |
|---|---|---|
| 21 | 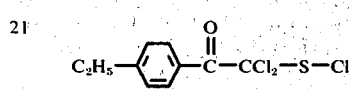 | 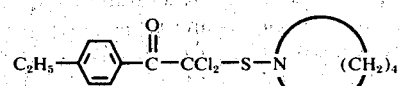 |
| 22 | 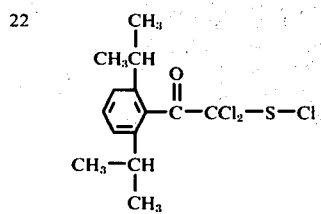 | 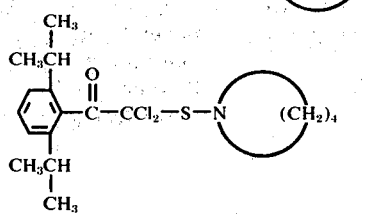 |
| 23 | 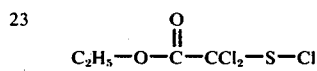 | 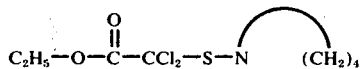 |
| 24 | 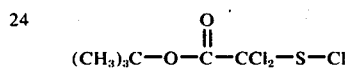 | 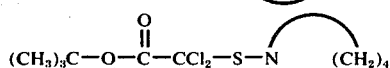 |
| 25 | 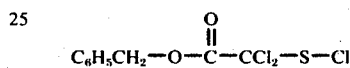 | 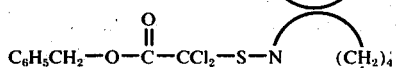 |
| 26 | 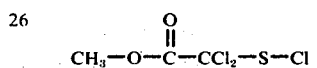 | 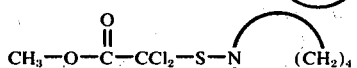 |
| 27 | 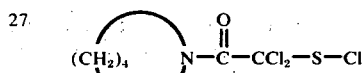 |  |
| 28 | 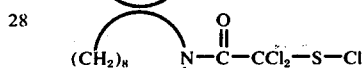 | 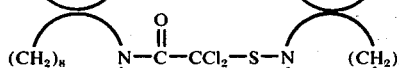 |
| 29 | 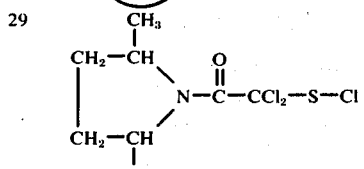 | 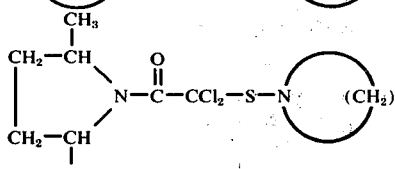 |
| 30 | 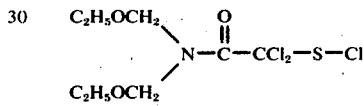 | 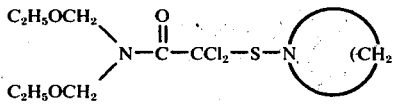 |
| 31 | 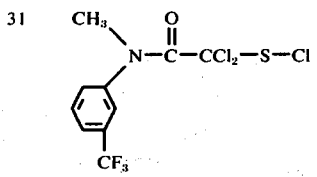 | 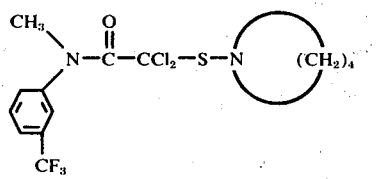 |
EXAMPLES 32 through 37
The procedure of Example 1 is followed except that, in place of about 2.52 g. of pyrrolidine, an approximately equimolecular amount of the compound of Column A is charged and the product of Column B is obtained.
| Example | A | B |
|---|---|---|
| 32 | $C_6H_5NH_2$ | 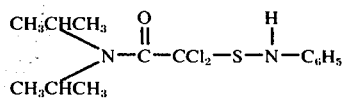 |

-continued

| Example | A | B |
|---|---|---|
| 33 | 2,6-dichlorophenyl with CH₂-O-CH₃ and NH | (CH₃CHCH₃)₂N-C(=O)-CCl₂-S-N(CH₂OCH₃)(2,6-dichlorophenyl) |
| 34 | 3-bromophenyl-NH-C₂H₅ | (CH₃CHCH₃)₂N-C(=O)-CCl₂-S-N(C₂H₅)(3-bromophenyl) |
| 35 | 2-CF₃-phenyl-NH-CH₃ | (CH₃CHCH₃)₂N-C(=O)-CCl₂-S-N(CH₃)(2-CF₃-phenyl) |
| 36 | 4-(CH₃)₃C-phenyl-NH-C₂H₄OC₂H₅ | (CH₃CHCH₃)₂N-C(=O)-CCl₂-S-N(C₂H₄OC₂H₅)(4-C(CH₃)₃-phenyl) |
| 37 | 2,4,6-trimethylphenyl-N(H)(CH₂OC₄H₉) | (CH₃CH(CH₃))₂N-C(=O)-CCl₂-S-N(CH₂OC₄H₉)(2,4,6-trimethylphenyl) |

EXAMPLE 38

The procedure of Example 1 is followed except that, instead of removing the precipitate from the reaction mass, by filtration after cooling, about 200 ml. of water are added to the mass upon cooling and the mass is stirred until the precipitate is no longer visible. The mass then separates into an organic and an aqueous phase, the aqueous phase, which contains the dissolved precipitate, is removed and the organic phase is then processed as in Example 1. The product of Example 1 is obtained.

EXAMPLES 39 and 40

The procedure of Example 1 is followed except that the amount of pyrrolidine added is approximately 1.26 g., about 0.02 moles, and, in addition, about 0.02 moles of the specified trialkyl amine is added with the pyrrolidine. The product of Example 1 is obtained.
Example 39 - Triethylamine.
Example 40 - Tributylamine.

EXAMPLE 41

Contact herbicidal activity of representative substituted dichlorosulfenamides of this invention is determined by the following procedure:

The compound to be tested is applied in spray form to plants of a given age of several grasses and broadleaf species. After the plants are the desired age, each aluminum pan is sprayed with a given volume of a 0.5% concentration solution of the candidate chemical, corresponding to a rate of approximately 10 lbs. per acre. This solution is prepared from an aliquot of a 2% solution of the candidate compound in acetone, a known amount of cyclohexanone-emulsifying agent mix, and sufficient water to make up to volume. The emulsifying agent is a mixture comprising 35 wt. percent butylamine dodecylbenzene sulfonate and 65 wt. percent of a tall oil-ethylene oxide condensate having about 6 moles of ethylene oxide per mole of tall oil. The injuries to the plants are then observed approximately 14 days later and the results are recorded.

Contact herbicidal activity of the compounds prepared in the designated Examples is observed against the species as shown in Table I. X denotes that herbicidal activity is observed. - denotes that the species was not tested.

TABLE 1

| Compound of Example Number | 4 | 7 | 9 |
|---|---|---|---|
| Canada thistle | | X | — |
| Cocklebur | | X | |
| Lambsquarter | X | | X |
| Smartweed | | X | |

EXAMPLE 42

Pre-emergent herbicidal activity of representative substituted dichlorosulfenamides of this invention is determined by the following procedure:

A good grade of top soil is placed in aluminum pans and compacted to a depth of ⅜ to ½ inch from the top of the pan. A pre-determined number of seeds of each of several plant species are placed on top of the soil in the pans. The seeds are covered with soil and the pans leveled. The herbicidal composition is applied by spraying the surface of the top layer of soil with a solution containing a sufficient amount of active ingredient to obtain a rate of applicaion of 5 lbs. per acre. The pans are then placed on a sand bench in the greenhouse and watered from below as needed. The plants are observed at the end of approximately 14 days and the results recorded.

Pre-emergent activity of the compounds prepared in the designated Examples is observed against the species as shown in Table II. X denotes that herbicidal activity is observed. - denotes that the species was not tested.

TABLE II

| Compound of Example Number | 1 | 2 | 4 | 5 | 6 | 9 | 10 | 11 | 12 | 13 |
|---|---|---|---|---|---|---|---|---|---|---|
| Canada thistle | X | X | | X | | | X | | | |
| Cocklebur | | | | | | X | | X | | |
| Velvet leaf | | | | X | | | | | — | — |
| Morning glory | | X | X | | | | | X | X | |
| Lambsquarter | | X | | X | X | | | | X | |
| Smartweed | — | — | X | | X | — | | — | X | |
| Nutsedge | | | | | | | | | X | |
| Quack grass | X | X | | | | | | | X | |
| Johnson grass | X | X | | X | | | | | X | |
| Bromegrass (cheat) | | | | | | | X | | X | X |
| Barnyard grass | | | | X | X | X | | | X | X |

While this invention has been described with respect to certain embodiments it is to be understood that it is not so limited and that variations and modifications thereof obvious to those skilled in the art to which this invention appertains can be made without departing from the spirit or scope thereof.

What is claimed is:

1. A substituted dichlorosulfenamide of the formula

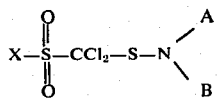

wherein X is phenyl, halophenyl or lower alkylphenyl and A and B when taken together are alkylene of the empirical formula $C_nH_{2n}$ wherein n is an integer from 4 through 8, inclusive, and having from 4 through 8 carbons in a continuous chain between the nitrogen terminal valence bonds.

2. The compound of claim 1 which is

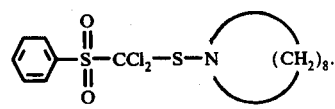

* * * * *